United States Patent
Barta

(10) Patent No.: US 10,004,743 B2
(45) Date of Patent: Jun. 26, 2018

(54) PROCESS FOR DRYING OF BIBW2992, OF ITS SALTS AND OF SOLID PHARMACEUTICAL FORMULATIONS COMPRISING THIS ACTIVE INGREDIENT

(71) Applicant: Boehringer Ingelheim International GmbH, Ingelheim am Rhein (DE)

(72) Inventor: Albert Barta, Warthausen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days. days.

(21) Appl. No.: 15/371,252

(22) Filed: Dec. 7, 2016

(65) Prior Publication Data

US 2017/0079980 A1    Mar. 23, 2017

Related U.S. Application Data

(62) Division of application No. 13/378,379, filed as application No. PCT/EP2010/059546 on Jul. 5, 2010, now Pat. No. 9,545,381.

(30) Foreign Application Priority Data

Jul. 6, 2009 (EP) .................................... 09164659
Feb. 24, 2010 (EP) .................................... 10154562

(51) Int. Cl.
| A61K 31/4375 | (2006.01) |
| A61K 9/00 | (2006.01) |
| A61K 9/28 | (2006.01) |
| A61K 31/517 | (2006.01) |
| A61K 9/16 | (2006.01) |
| A61K 9/20 | (2006.01) |

(52) U.S. Cl.
CPC .......... *A61K 31/517* (2013.01); *A61K 9/1641* (2013.01); *A61K 9/1652* (2013.01); *A61K 9/2009* (2013.01); *A61K 9/2013* (2013.01); *A61K 9/2018* (2013.01); *A61K 9/2027* (2013.01); *A61K 9/2054* (2013.01); *A61K 9/2095* (2013.01); *A61K 9/2813* (2013.01); *A61K 9/2826* (2013.01); *A61K 9/2853* (2013.01); *A61K 9/2866* (2013.01)

(58) Field of Classification Search
None
See application file for complete search history.

(56) References Cited

U.S. PATENT DOCUMENTS

| 4,933,443 A | 6/1990 | Hamashima et al. |
| 5,728,687 A | 3/1998 | Bissery |
| 5,866,572 A | 2/1999 | Barker et al. |
| 6,127,374 A | 10/2000 | Bridges |
| 6,153,617 A | 11/2000 | Bridges |
| 6,217,866 B1 | 4/2001 | Schlessinger et al. |
| 6,251,912 B1 | 6/2001 | Wissner et al. |
| 6,297,258 B1 | 10/2001 | Wissner et al. |
| 6,344,459 B1 | 2/2002 | Bridges et al. |
| 6,362,336 B1 | 3/2002 | Lohmann et al. |
| 6,403,580 B1 | 6/2002 | Himmelsbach et al. |
| 6,617,329 B2 | 9/2003 | Himmelsbach et al. |
| 6,627,634 B2 | 9/2003 | Himmelsbach et al. |
| 6,653,305 B2 | 11/2003 | Himmelsbach et al. |
| 6,656,946 B2 | 12/2003 | Himmelsbach et al. |
| 6,673,803 B2 | 1/2004 | Thomas et al. |
| 6,740,651 B2 | 5/2004 | Himmelsbach et al. |
| 6,924,285 B2 | 8/2005 | Himmelsbach et al. |
| 6,972,288 B1 | 12/2005 | Himmelsbach et al. |
| 7,019,012 B2 | 3/2006 | Himmelsbach et al. |
| 7,084,136 B2 | 8/2006 | Tanimoto et al. |
| 7,119,084 B2 | 10/2006 | Himmelsbach et al. |
| 7,160,889 B2 | 1/2007 | Hennequin et al. |
| 7,196,091 B2 | 3/2007 | Himmelsbach et al. |
| 7,220,750 B2 | 5/2007 | Himmelsbach et al. |
| 7,223,749 B2 | 5/2007 | Himmelsbach et al. |
| 7,456,189 B2 | 11/2008 | Himmelsbach et al. |
| 7,846,936 B2 | 12/2010 | Hilberg et al. |
| 7,960,546 B2 | 6/2011 | Schroeder et al. |
| 8,067,593 B2 | 11/2011 | Schroeder et al. |
| RE43,431 E | 5/2012 | Himmelsbach et al. |
| 8,188,274 B2 | 5/2012 | Schroeder et al. |
| 8,404,697 B2 | 3/2013 | Solca et al. |
| 8,545,884 B2 * | 10/2013 | Messerschmid ..... A61K 9/0095 264/109 |
| 8,828,391 B2 | 9/2014 | Denis et al. |
| 8,877,764 B2 | 11/2014 | Solca |
| 9,089,571 B2 | 7/2015 | Solca et al. |
| 9,539,258 B2 | 1/2017 | Solca et al. |
| 2001/0044435 A1 | 11/2001 | Himmelsbach et al. |
| 2002/0032208 A1 | 3/2002 | Lohmann et al. |
| 2002/0077330 A1 | 6/2002 | Himmelsbach et al. |

(Continued)

FOREIGN PATENT DOCUMENTS

| CN | 103755688 A | 4/2014 |
| DE | 19825591 A1 | 12/1999 |

(Continued)

OTHER PUBLICATIONS

"Afatinib Prolongs Progression-Free Survival in NSCLC", 2012 ASCO Annual Meeting, Chicago, ASCO Daily News, LBA7500, Jun. 1-5, 2012. [downloaded from the internet Oct. 25, 2012. http://chicago2012.asco.org/ASCODailyNews/LBA7500.aspx].

(Continued)

*Primary Examiner* — Robert T. Crow
*Assistant Examiner* — John P Nguyen
(74) *Attorney, Agent, or Firm* — Marc A. Began; Atabak R. Royaee

(57) ABSTRACT

The present invention relates to a drying process of BIBW 2992 or the salts thereof, preferably the dimaleate salt, as well as of solid pharmaceutical formulations comprising BIBW2992 or a salt thereof, and to pharmaceutical compositions comprising BIBW 2992 or a salt thereof as the active product ingredient, characterized by a water activity of the formulation of not more than 0.20 or a water content (Karl-Fischer) of not more than 4.2%.

5 Claims, 2 Drawing Sheets

(56) References Cited

U.S. PATENT DOCUMENTS

| | | |
|---|---|---|
| 2002/0082270 A1 | 6/2002 | Himmelsbach et al. |
| 2002/0169180 A1 | 11/2002 | Himmelsbach et al. |
| 2002/0173509 A1 | 11/2002 | Himmelsbach et al. |
| 2002/0198160 A1 | 12/2002 | Everitt et al. |
| 2003/0149062 A1 | 8/2003 | Jung et al. |
| 2003/0186956 A1 | 10/2003 | Bilke et al. |
| 2003/0191308 A1 | 10/2003 | Hennequin et al. |
| 2003/0225079 A1 | 12/2003 | Singer et al. |
| 2004/0024019 A1 | 2/2004 | Tanimoto et al. |
| 2004/0057992 A1 | 3/2004 | Gierer |
| 2004/0158065 A1 | 8/2004 | Barth et al. |
| 2005/0031769 A1 | 2/2005 | Watanabe et al. |
| 2005/0043233 A1 | 2/2005 | Stefanic et al. |
| 2005/0085495 A1 | 4/2005 | Soyka et al. |
| 2005/0215574 A1 | 9/2005 | Bradbury et al. |
| 2006/0058311 A1 | 3/2006 | Munzert et al. |
| 2006/0100223 A1 | 5/2006 | Himmelsbach et al. |
| 2006/0270672 A1 | 11/2006 | Himmelsbach et al. |
| 2007/0009533 A1 | 1/2007 | Sikic et al. |
| 2007/0027170 A1 | 2/2007 | Soyka et al. |
| 2007/0078091 A1 | 4/2007 | Hubler et al. |
| 2007/0099918 A1 | 5/2007 | Singer et al. |
| 2007/0185091 A1 | 8/2007 | Himmelsbach et al. |
| 2008/0096212 A1 | 4/2008 | Bell et al. |
| 2008/0103161 A1 | 5/2008 | Himmelsbach et al. |
| 2008/0145422 A1 | 6/2008 | Zhou et al. |
| 2008/0207615 A1 | 8/2008 | Bell et al. |
| 2008/0234264 A1 | 9/2008 | Bell et al. |
| 2008/0254040 A1 | 10/2008 | Stefanic et al. |
| 2008/0269487 A1 | 10/2008 | Bradbury et al. |
| 2009/0036676 A1 | 2/2009 | Himmelsbach et al. |
| 2009/0203683 A1 | 8/2009 | Himmelsbach et al. |
| 2009/0238828 A1 | 9/2009 | Munzert et al. |
| 2009/0306044 A1 | 12/2009 | Solca et al. |
| 2009/0306072 A1 | 12/2009 | Jung et al. |
| 2009/0306101 A1 | 12/2009 | Solca et al. |
| 2009/0306378 A1 | 12/2009 | Schroeder et al. |
| 2009/0318480 A1 | 12/2009 | Solca |
| 2010/0010023 A1 | 1/2010 | Himmelsbach et al. |
| 2010/0069414 A1 | 3/2010 | Himmelsbach et al. |
| 2010/0087482 A1 | 4/2010 | Haber et al. |
| 2010/0144639 A1 | 6/2010 | Singer et al. |
| 2011/0039863 A1 | 2/2011 | Hilberg et al. |
| 2011/0046168 A1 | 2/2011 | Himmelsbach et al. |
| 2011/0136826 A1 | 6/2011 | Hilberg et al. |
| 2011/0142929 A1 | 6/2011 | Messerschmid et al. |
| 2011/0171289 A1 | 7/2011 | Stefanic et al. |
| 2011/0207929 A1 | 8/2011 | Schroeder et al. |
| 2011/0207932 A1 | 8/2011 | Schroeder et al. |
| 2012/0046494 A1 | 2/2012 | Choi et al. |
| 2012/0107399 A1 | 5/2012 | Barta |
| 2012/0157472 A1 | 6/2012 | Larsen et al. |
| 2012/0294867 A1 | 11/2012 | Denis et al. |
| 2012/0329778 A1 | 12/2012 | Himmelsbach et al. |
| 2013/0012465 A1 | 1/2013 | Haslinger et al. |
| 2017/0312360 A1 | 11/2017 | Denis et al. |

FOREIGN PATENT DOCUMENTS

| | | |
|---|---|---|
| DE | 19908567 A1 | 8/2000 |
| DE | 19911366 A1 | 9/2000 |
| DE | 10017539 A1 | 10/2001 |
| DE | 10042060 A1 | 3/2002 |
| DE | 10042064 A1 | 3/2002 |
| EP | 0302967 A2 | 2/1989 |
| EP | 0566226 A1 | 10/1993 |
| EP | 0799619 A2 | 10/1997 |
| EP | 1123705 A1 | 8/2001 |
| EP | 2612860 A1 | 7/2013 |
| WO | 199410995 A1 | 5/1994 |
| WO | 9428880 A1 | 12/1994 |
| WO | 199520045 A1 | 7/1995 |
| WO | 199630347 A1 | 10/1996 |
| WO | 199633980 A1 | 10/1996 |
| WO | 199702266 A1 | 1/1997 |
| WO | 199738983 A1 | 10/1997 |
| WO | 199843960 A1 | 10/1998 |
| WO | 199906378 A1 | 2/1999 |
| WO | 199906396 A1 | 2/1999 |
| WO | 199909016 A1 | 2/1999 |
| WO | 199935146 A1 | 7/1999 |
| WO | 1999065228 A2 | 12/1999 |
| WO | 200018740 A1 | 4/2000 |
| WO | 200031048 A1 | 6/2000 |
| WO | 200031068 A1 | 6/2000 |
| WO | 200051991 A1 | 9/2000 |
| WO | 200055141 A1 | 9/2000 |
| WO | 200078735 A1 | 12/2000 |
| WO | 200134574 A1 | 5/2001 |
| WO | 200168186 A2 | 9/2001 |
| WO | 200177104 A1 | 10/2001 |
| WO | 200218351 A1 | 3/2002 |
| WO | 200218372 A1 | 3/2002 |
| WO | 200218373 A1 | 3/2002 |
| WO | 200218375 A1 | 3/2002 |
| WO | 200218376 A1 | 3/2002 |
| WO | 200241882 A2 | 5/2002 |
| WO | 200250043 A1 | 6/2002 |
| WO | 2003082290 A1 | 10/2003 |
| WO | 2003089439 A1 | 10/2003 |
| WO | 2003094921 A2 | 11/2003 |
| WO | 2004014426 A1 | 2/2004 |
| WO | 2004066919 A2 | 8/2004 |
| WO | 2004074263 A1 | 9/2004 |
| WO | 2004096224 A2 | 11/2004 |
| WO | 2004108664 A2 | 12/2004 |
| WO | 2005023315 A2 | 3/2005 |
| WO | 2005028470 A1 | 3/2005 |
| WO | 2005030179 A1 | 4/2005 |
| WO | 2005033096 A1 | 4/2005 |
| WO | 2005037824 A2 | 4/2005 |
| WO | 2005094357 A2 | 10/2005 |
| WO | 2006017317 A2 | 2/2006 |
| WO | 2006018182 A1 | 2/2006 |
| WO | 2006084058 A2 | 8/2006 |
| WO | 2006127207 A1 | 11/2006 |
| WO | 2007054550 A1 | 5/2007 |
| WO | 2007054551 A1 | 5/2007 |
| WO | 2007085638 A1 | 8/2007 |
| WO | 2008034776 A1 | 3/2008 |
| WO | 2008091701 A2 | 7/2008 |
| WO | 2009030239 A1 | 3/2009 |
| WO | 2009137429 A1 | 11/2009 |
| WO | 2009147238 A1 | 12/2009 |
| WO | 2010048477 A2 | 4/2010 |
| WO | 2010081817 A1 | 7/2010 |
| WO | 2010085845 A1 | 8/2010 |
| WO | 2010129053 A2 | 11/2010 |
| WO | 2011003853 A2 | 1/2011 |
| WO | 2011056894 A2 | 5/2011 |
| WO | 2011069962 A1 | 6/2011 |
| WO | 2012156437 A1 | 11/2012 |
| WO | 2013173254 A1 | 11/2013 |

OTHER PUBLICATIONS

Abstract in English (2000) for DE19911366.
Abstract in English for WO199965228, 2010.
Agus, D.B. et al., Abstract: "A phase I dose escalation study of BIBW 2992, an irreversible dual EGFR/HER2 receptor tyrosine kinase inhibitor, in a continuous schedule in patients with advanced solid tumours." Journal of Clinical Oncology, 2006, ASCO Annual Meeting Proceedings (Post-Meeting Edition). vol. 24, No. 18S, (Jun. 20 Supplement), 2006, 2074.
Alan, R. "Benign Prostatic Hyperplasia (BPH)". Available at http://healthlibrary.epnet.com/GetContent/asp?token-1baaea3c-d4f5-4e14-8429-e3b3e1add7a7&chunkiid-1203, last reviewed Mar. 2006.
Argiris, A. et al., "Phase III Randomized, Placebo-Controlled Trial of Docetaxel With or Without Gefitinib in Recurrent or Metastatic Head and Neck Cancer: An Eastern Cooperative Oncology Group Trial." Journal of Clinical Oncology, 2013, vol. 31, No. 11, pp. 1405-1414.

(56) References Cited

OTHER PUBLICATIONS

Barton, J. et al., "Growth Factors and their Receptors: new Targets for Prostate Cancern Therapy". Urology 58 (Supplement 2A), Aug. 2001, p. 114-122.
Bell, D.W. et al., "Inherited susceptibility to lung cancer may be associated with the T790M drug resistance mutation in EGFR". Nature Genetics, Dec. 2005, vol. 37, No. 12, p. 1315-1316. Published online Oct. 30, 2005.
Boehringer Ingelheim Press Release "Resistance to Epidermal Growth Factor Receptor (EGFR) Tyrosine Kinase Inhibitors (TKIs)." 2010.
Boehringer Ingelheim, "BIBW 2992: A Potent and Irreversible Inhibitor of EGFR/HER1 and HER2." Accessed on Jan. 3, 2012.
Boschelli, D., "4-Anilino-3-quinolinecarbonitriles: An Emerging Class of Kinase Inhibitors—An Update." Medicinal Chemistry Reviews—Online, 2004, vol. 1, pp. 457-463.
Burris, HA et al.; "EGF1004: a randomized, multicenter, phase Ib study of the safety, biologic activity and clinical efficacy of the dual kinase inhibitor GW572016" Breast Cancer Research and Treatment, V. 82, suppl. 1 (2003), p. S18 #39.
Calabrisi, P. et al., Goodman * Gilman. "Section IX Chemotherapy of Neoplastic Diseases—Introduction". Goodman & Gilman's The Pharmacological Basis of Therapeutics, 10th ed, 2001, Hardman, JG, Limbird LE, Gilman AG, Eds. McGraw-Hill, NY, 2001, p. 1381-1388 (pp. 1381m 1383-1385 and 1388 provided).
Camp, E. et al., "Molecular Mechanisms of Resistance to Therapies Targeting the Epidermal Growth Factor Receptor." Clinical Cancer Research, 2005, vol. 11, No. 1, pp. 397-405.
Cancer Genome and Collaborative Group. Nature, Brief Communications Sep. 2004, vol. 431, p. 525-526.
Carter, T.A. et al., "Inhibition of drug-resistant mutants of ABL, KIT, and EGF receptor kinases." Proceedings of National Academy of Sciences of the USA, 2005, vol. 102, No. 31, pp. 11011-11016.
Cascone, T. et al, "Epidermal growth factor receptor inhibitors in non-small-cell lung cancer", Expert Opinion on Drug Discovery, Informa Healthcare, London, GB, vol. 2, No. 3, Mar. 1, 2008, p. 335-348.
Chan, S.K. et al., "Mutations of the epidermal growth factor receptor in non-small cell lung cancer—Search and destroy." European Journal of Cancer 42, 2006, pp. 17-23.
Choong, N. et al., "Gefitinib Response of Erlotinib-refractory Lung Cancer Involving Meninges—Role of EGFR Mutation." Nature Clinical Practice Oncology, 2006, vol. 3, No. 1, pp. 50-57.
Chustecka, Zosia, "Afatinib Shows Modest Benefit in Head and Neck Cancer." Boehringer Ingelheim, European Society for Medical Oncology (ESMO) Congress 2014, Presented Sep. 27, 2014, Medscape.com.
deMiguel, M. et al., "Immunohistochemical comparative analysis of transforming grwoth factor a, epidermal growth factor, and epidermal growth factor receptor in normal, hyperplastic and neoplastic human prostates". Cytokine, 1998, p. 722-727.
Doebele, R. et al., "New strategies to overcome limitations of reversible EGFR tyrosine kinase inhibitor therapy in non-small cell lung cancer." Lung Cancer, 2010, vol. 69, pp. 1-12.
Drug Data Report, "BIBW-2992" 2005, vol. 27, No. 11.
Duque, J.L. et al., "Heparin-Binding Epidermal Growth Factor-Like Growth Factor is an Autocrine Mediator of Human Prostate Stromal Cell Growth in Vitro". The Journal of Urology, vol. 165, Jan. 2001, p. 284-288.
European Society for Medical Oncology, "ESMO 2014 Press Release: Second-Line Afatinib Significantly Improves Progression-Free Survival in Recurrent or Metastatic Head and Neck Cancer, Phase III Trial Shows." Retrieved online Dec. 18, 2014. http://www.esmo.org/Conferences/ESMO-2014-Congress/Press-Media/Second-Line-Afatinib-Significantly-Improves-Progression-Free-Survival-in-Recurrent-or-Metastatic-Head-and-Neck-Cancer-Phase-III-Trial-Shows.
European Society for Medical Oncology, "ESMO 2014: Afatinib vs Methotrexate in Second-Line Treatment of Recurrent and/or Metastatic Head and Neck Squamos Cell Carcinoma." Retrieved online Dec. 18, 2014. http://www.esmo.org/Conferences/ESMO-2014-Congress/News-Articles/Afatinib-vs-Methotrexate-in-Second-Line-Treatment-of-Recurrent-and-or-Metastatic-Head-and-Neck-Squamous-Cell-Carcinoma.
Fry, David W., "Inhibition of the Epidermal Growth Factor Receptor Family of Tyrosine Kinases as an Approach to Cancer Chemotherapy Progression from Reversible to Irreversible Inhibitors." Pharmacological & Therapeutics, 1999, vol. 82, No. 2-3, pp. 207-218.
Gonzales-Barcena, D. et al., "Responses to the antagonistic analog of LH-RH (SB-75, cetrorelix) in patients with benign prostatic hyperplasia and prostatic cancer". The Prostate, 1994, 24(2), p. 84-92, only abstract provided.
Goodman & Gilman's, "The Pharmacological Basis of Therapeutics" Tenth Edition, 2001, pp. 1381-1388.
Hansen, A.R. et al., "Epidermal Growth Factor Receptor Targeting in Head and Neck Cancer: Have We Been Just Skimming the Surface?" Journal of Clinical Oncology, 2013, vol. 31, No. 11, pp. 1381-1383.
Harari, P.M. "Epidermal growth factor receptor inhibition strategies in oncology". Endocrine-Related Cancer, 2004, vol. 11. p. 689-708.
Herbst, R.S. et al., "Monoclonal Antibodies to Target Epidermal Growth Factor Receptor-Positive Tumors". Cancer, Mar. 1, 2002, vol. 94, No. 5, p. 1593-1611.
Hirsh, V., "Afatinib (BIBW 2992) Development in Non-Small-Cell Lung Cancer." Future Oncology, 2011, vol. 7, pp. 317-825.
Hofmann, B .B., Chapter 10 Catecholamines, Sympathomimetic Drugs, and Adrenergic Receptor Antagonists. "Goodman and Gilman's The Pharmacological Basis of Therapeutics, 10th ed." Hardman JG, Limbird, LE, and Gilman AG, Eds. McGraw-Hill, 2001, p. 215-268, pp. 215, 247 and 248 provided).
International Search Report and Written Opinion for PCT/EP2006/068313 dated Feb. 26, 2007.
International Search Report and Written Opinion for PCT/EP2007/059735 dated Dec. 6, 2007.
International Search Report and Written Opinion for PCT/EP2010/059546 dated Nov. 22, 2011.
International Search Report and Written Opinion for PCT/EP2012/059098 dated Jun. 27, 2012.
International Search Report for PCT/EP01/14569 dated Mar. 1, 2002.
Janjigian, Y. et al., "Phase I/II Trial of Cetuximab and Erlotinib in Patients with Lung Adenocarcinoma and Acquired Resistance to Erlotinib." Clinical Cancer Research, 2011, vol. 17, No. 8, pp. 2521-2527.
Johnson, J, et al. "Relationships between drug activity in NCI preclinical in vitro and in vitro and in vivo models and early clinical trials". British Journal of Cancer, 2001, 84 (10, p. 1424-1431.
Kawabata, S. et al., "Abstract 2417: A new mouse model for epithelial ear neoplasms based upon expression of mutant EGFRL858R/T790M." Cancer Research, 2011, vol. 71, No. 8, p. 1.
Kobayashi, S. et al.,"EGFR Mutation and Resistance of Non-Small-Cell Lung Cancer to Gefitinib." The New England Journal of Medicine, 2005, vol. 352, pp. 786-792.
Krozely, P. Abstract—Clinical Journal of Oncology Nursing, 2004, vol. 8, No. 2, p. 1092-1095.
Kwak, E. et al. "Irreversible Inhibitors of the EGF Receptor may Circumvent Acquired Resistance to Gefitinib." PNAS, 2005, vol. 102, No. 21, pp. 7665-7670.
Kwak, E.L et al., "Irreversible inhibitors of the EGF receptor may circumvent acquired resistance of gefitinib." Proceedings of National Academy of Sciences of the USA, 2005, vol. 102, No. 21, pp. 7665-7670.
Laird & Cherrington, "Small molecule tyrosine kinase inhibitors: clinical development of anticancer agents" Expert Opinion. Investig. Drugs.; Ashley Publications (2003) 12(1) p. 51-64.
Lee, M., "Tamsulosin for the Treatment of Benigh Prostatic Hypertrophy". The Annals of Pharmacotherapy, Feb. 2000, 34, p. 188-199.
Lewis, N., et al. Abstract: "A phase I dose escalation study of BIBW 2992, an irreversible dual EGFR/HER2 receptor tyrosine kinase inhibitor, in a 3 week on 1 week off schedule in patients with advanced solid tumors". Journal of Clinical Oncology, 2006 ASCO

(56) References Cited

OTHER PUBLICATIONS

Annual Meeting Proceedings (Post-Meeting Edition). vol. 24, No. 18S (Jun. 20 Supplement), 2006: 3091.
Li, D. et al. "BIBW2992, An Irreversible EGFR/HER2 Inhibitor Highly Effective in Preclinical Lung Cancer Models." Oncogene, 2008, vol. 27, No. 34, pp. 4702-4711.
Martins, R.G. et al., "Cisplatin and Radiotherapy With or Without Erlotinib in Locally Advanced Squamous Cell Carcinoma of the Head and Neck: A Randomized Phase II Trial." Journal of Clinical Oncology, 2013, vol. 31, No. 11, pp. 1415-1421.
McMahon; VEGF Receptor Signaling in Tumor Angiogenesis; The Oncologist; 2000; 5 (suppl 1); pp. 3-10.
Miller, V.A., et al., "Afatinib versus placebo for patients with advanced, metastatic non-small-cell lung cancer after failure of erlotinib, gefitinib, or both, and one or two lines of chemotherapy (LUX-Lung1): a phase 2b/3 randomised trial", The Lancet, Oncology, vol. 19, May 2012, pp. 528-538.
Mills; Humidity Control in Pharma Processing; Innovations in Pharmaceutical Technology; 2007; pp. 1-3.
Nosov et al., "Mekhanismy regulyatsii vnutrikletochnoi peredachi signala . . . " VIII Rossiiskii Onkologicheskii Congress—Moscow, 2004.
Paez, J. G. "EGFR Mutations in Lung Cancer: Correlation with Clinical Response to Gefitinib Therapy". Science, vol. 304, 2004, p. 1497-1500.
Pinedo et al.; Translational Research: The Role of VEGF in Tumor Angiogenesis; The Oncologist; 2000; 5(suppl 1); pp. 1-2.
Plummer et al.; 573 Poster Phase I study of BIBW2992, an oral irreversible dual EGFR/HER2 inhibitor, showing activity in tumors with mutated EGFR; European Journal of Cancer; Supplement; Nov. 2006; vol. 4; No. 12; Pergamon; Oxford, GB.
Prescribing Information, Package insert for Erbitux, Revised Jul. 2009, pp. 1-24.
Ramalingam, S. et al., "Dual Inhibition of the Epidermal Growth Factor Receptor with Cetuximab, an IgG1 Monoclonal Antibody, and Gefitinib, A Tyrosine Kinase Inhibitor, in Patients with Refractory Non-small Cell Lung Cancer (NSCLC): A Phase I Study." Journal of Thoracic Oncology, 2008, vol. 3, No. 3, pp. 258-264.
Rayford, W. et al., "Muscarinic Cholinergic Receptors Promote Growth of Human Prostate Cancer Cells". The Prostate, Feb. 1997, 30(3), p. 160-165.
Regales, L. et al., "Dual targeting of EGFR can overcome a major drug resistance mutation in mouse models of EGFR mutant lung cancer", American Society for Clinical Investigation, vol. 199, No. 10, Oct. 1, 2009, p. 3000-3010.
Reid, A, et al, "Dual inhibition of ErbB1 (EGFR/HER1) and ErbB2 (HER2/neu)", European Journal of Cancer, Pergamon Press, Oxford, GB, vol. 43, No. 3, Feb. 1, 2008, p. 481-489.
Rosell, R. et al., "Crossing the Rubicon in Lung Adenocarcinoma: the Conundrum of EGFR Tyrosine Kinase Mutations." 2005, vol. 1, No. 3, pp. 319-322.
Sausville, E. A. et al. "Contributions of Human Tumor Xenografts to Anticancer Drug Development". Cancer Research, 2006, vol. 66 (7), p. 3351-3354.
Seiwert, T.Y. et al., "A randomized, phase II study of afatinib versus cetuximab in metastatic or recurrent squamous cell carcinoma of the head and neck." Annals of Oncology, 2014, vol. 25, No. 9, pp. 1813-1820.
Sequist, L.V. et al., "1229PD / Lux-Lung 3: Symptom and Health-Related Quality of Life Results from a Randomized Phase III Study in 1st-Line Advanced NSCLC Patients Harbouring EGFR Mutations", Poster Discussion, Sep. 30, 2012 [downloaded from the internet Oct. 25, 2012. http://abstracts.webges.com/myitinerary/session-148.html?congress=esmo2012#.UFdGtBr1LSY.gmai].
Sequist, L.V. et al., "Neratinib, an Irreversible Pan-ErbB Receptor Tyrosine Kinase Inhibitor: Results of a Phase II Trial in Patients With Advanced Non-Small-Cell Lung Cancer." Journal of Clinical Oncology, 2010, vol. 28, No. 18, pp. 3076-3083.
Sequist, L.V., et al., "Neratinib, an Irrerversible Pan-ErbB Receptor Tyrosine Kinase Inhibitor: Results of a Phase II Trial in Patients with Advanced Non-Small-Cell Lung Cancer" Journal of Clinical Oncology, vol. 28, No. 18, Jun. 20, 2010, p. 3076-3083.
Solca et al., Abstracts of AACR-EORTC International Conference, Molecular Targets and Cancer Therapeutics.
Solca et al.; 567 Poster Efficacy of BIBW 2992, an irreversible dual EGFR/HER2 receptor tyrosine kinase Inhibitor, in combination with cytotoxic agents; European Journal of Cancer; Supplement; Nov. 2006; vol. 4; No. 12; Pergamon; Oxford, GB.
Solca, F. et al., "A242 BIBW 2992, an Irreversible Dual EGFR/HER2 Kinase Inhibitor, Shows Activity on L858R/T790M EGFR Mutants." and "A244 BIBW 2992, An Irreversible Dual EGFR/HER2 Receptor Tyrosine Kinase Inhibitor for Cancer Therapy." Molecular Targets and Cancer Therapeutics, Nov. 2005.
Stedman's Medical Dictionary, 27th edition, Lippincott, Williams & Wilkins, Baltimore, 2000.
Subramaniam, D.S. et al., "BIBW 2992 in non-small cell lung cancer". Expert Opinion Investig. Drugs, 2011, 20(3), p. 415-422.
Supplement ASCO Meeting Abstracts 1-4, Journal of Clinical Oncology, 2006.
Toyooka, S. et al., "EGFR Mutation and Response of Lung Cancer to Gefitinib." The New England Journal of Medicine, 2005, vol. 352, No. 20, p. 2136.
Tsou, Hwei-Ru, "6-Substituted-4-(3-bromophenylamino)quinazolines as Putative Irreversible Inhibitors of the Epidermal Growth Factor Receptor (EGFR) and Human Epidermal Growth Facotr Receptor (HER-2) Tyrosine Kinases with Enhanced Antitumore Activity", J. Med. Chem 2001, 2719-2734, vol. 44.
U.S. Appl. No. 12/914,003, filed Oct. 28, 2010, Inventor: Frank Himmelsbach. (The cited pending U.S. application is stored in the USPTO IFW system (MPEP 609.04(a)(II)(C)).
Vlahovic, G., et al., "Activation of Tyrosine Kinases in Cancer", The Oncologist, 2003, vol. 8, pp. 531-538.
Wikstrand, C. et al. "Monoclonal Antibodies against EGFRvIII Are Tumor Specific and React with Breast and Lung Carcinomas and Malignant Gliomas." Cancer Research, 1995, vol. 55, No. 14, pp. 3140-3148.
Wissner, A. et al., "Synthesis and Structure—Activity Relationships of 6,7-Disubstituted 4-Anilinoquinoline-3-carbonitriles. The Design of an Orally Active, Irreversible Inhibitor of the Tyrosine Kinase Activity of the Epidermal Growth Factor Receptor (EGFR) and the Human Epidermal Growth Factor Receptor-2 (HER-2)." Journal of Medicinal Chemistry, 2003, vol. 46, pp. 49-63.
Xu, Y. et al., "Acquired Resistance of Lung Adenocarcinoma to EGFR-tyrosine Kinase Inhibitors Gefitinib and Erlotinib." Cancer Biology & Therapy, 2010, vol. 9, No. 8, pp. 572-582.
Yanase, K. et al., "Gefitinib reverses breast cancer resistance protein-medicated drug resistance". Molecular Cancer Therapeutics, 2004, Vo. 9, No. 9, p. 1119-1125.
Yang, J. C-H, et al., "Afatinib for patients with lung adenocarcinoma and epidermal growth factor receptor mutations (LUX-Lung 2): a phase 2 trial", The Lancet, Oncology, vol. 13, May 2012, pp. 539-548.
Yoshimura, N. et al., "EKB-569, a new irreversible epidermal growth factor recptor tyrosine kinase inhibitor, with clinical activity in patients with non-small cell lung cancer with acquired resistance to gefitinib." Lung Cancer, 2006, vol. 51, pp. 363-368.
Zhou, W. et al., "Novel mutant-selective EGFR kinase inhibitors against EGFR T790M." Nature, 2009, vol. 462, pp. 1070-1074.
Cetuximab—FDA Approval, Department of Health and Human Services Letter to ImClone Systems, Inc., dated Feb. 12, 2004.
Cetuximab—EMEA. Erbitux, EPAR (European Public Assessment Report) Summary for the Public, Doc. Ref.: EMEA/327144/2009. EMEA/H/C/558. Jun. 2009.
Cetuximab—Erbitux Label, 2004.
Humblet, Y. "Cetuximab: An IgG1 monoclonal antibody for the treatment of epidermal growth factor receptor-expressing tumours". Expert Opinion. Drug Evaluation. Ashley Publications, 2004, p. 1621-1633.
International Search Report and Written Opinion for PCT/EP2006/068314 dated Feb. 7, 2007.
National Cancer Institute, Cancer Drug Information, Cetuximab. Posted: Oct. 5, 2006, Updated: Dec. 30, 2010.

(56) References Cited

OTHER PUBLICATIONS

The Lancet, "Cetuximab in NSCLC: another trial needed." www.thelancet.com/oncology,. vol. 12, Jan. 2011.
International Search Report and Written Opinion for PCT/EP2014/051659 dated Sep. 5, 2014.
Gelovani, Juri G., "Molecular imaging of epidermal growth factor receptor expression-activity at the kinase level in tumors with positron emission tomography." Cancer and Metastasis Reviews, 2008, vol. 27, No. 4, pp. 645-653.
Seimbille, Y. et al., "Fluorine-18 labeling of 6,7-disubstituted anilinoquinazoline deratives for poistron emission tomography (PET) imaging of tyrosine kinase receptors: synthesis of 18F-Iressa and related molecular probes." Journal of Labelled Compounds and Radiopharmaceuticals, 2005, vol. 48, No. 11, pp. 829-843.
Slobbe, P. et al., "PET imaging with small-molecule tyrosine kinase inhibitors: TKI-PET." Drug Discovery Today, 2012, vol. 17, No. 21-22, pp. 1175-1187.
Stopfer, P. et al., "Afatinib pharmacokinetics and metabolism after oral administration to healthy male volunteers." Cancer Chemotherapy and Pharmacology, 2012, vol. 69, No. 4, pp. 1051-1061.
Agarwal et al.; Distribution of Gefitinib to the Brain Is Limited by P-glycoprotein (ABCB1) and Breast Cancer Resistance Protein (ABCG2)-Mediated Active Efflux; Journal of Pharmacology and Experimental Therapeutics; vol. 334; No. 1; Jul. 2010; pp. 147-155.
Chen et al.; Epidermal Growth Factor Receptor Inhibitors: Current Status and Future Directions; Current Problems in Cancer; Mosby, St. Louis, MO; vol. 33; No. 4; Jul. 1, 2009; pp. 245-294.
Chhun et al.; Gefitinib-phenytoin interaction is not correlated with the 14C-erythromycin breath test in healthy male volunteers; British Journal of Clinical Pharmacology; vol. 68; No. 2; Aug. 2009; pp. 226-237.
Collins et al.; Tyrosine kinase inhibitors potentiate the cytotoxicity of MDR-substrate anticancer agents independent of growth factor receptor status in lung cancer cell lines; Invest New Drugs; vol. 28; No. 4; Jun. 5, 2009; pp. 433-444.
Di Leo, A. et al., "Phase III, Double-Blind, Randomized Study Comparing Lapatinib Plus Paclitaxel With Placebo Plus Paclitaxel As First-Line Treatment for Metastatic Breast Cancer." Journal of Clinical Oncology, 2007, vol. 26, No. 34, pp. 5544-5552.
International Search Report, Form PCT/ISA/210 for corresponding PCT/EP2011/048922; dated Jan. 6, 2012.
Laack et al.; Lessons learnt from gefitinib and erlotinib: Key insights into small-molecule EGFR-targeted kinase Inhibitors in non-small cell lung cancer; Lung Cancer; vol. 69; No. 3; Sep. 1, 2010; pp. 359-264.
Lin; Drug-drug interaction mediated by inhibition and induction of P-glycoprotein; Advanced Drug Delivery Reviews; vol. 55; No. 1; Jan. 21, 2003; pp. 53-81.
Medina et al.; Lapatinib: A Dual Inhibitor of Human Epidermal Growth Factor Receptor Tyrosine Kinases; Clinical Therapeutics; vol. 30; No. 8; Aug. 2008; pp. 1426-1447.
Minkovsky et al.; BIBW-2992, a dual receptor tyrosine kinase inhibitor for the treatment of solid turmors; Current Opinion in Investigational Drugs, Pharmapress; vol. 9; No. 12; Dec. 1, 2008; pp. 1336-1346.

Shi, Zhi et al., "Inhibiting the function of ABCB1 and ABCG2 by the EGFR tyrosine kinase inhibitor AG1478." Biochemical Pharmacology, 2009, vol. 77, pp. 781-793.
Swaisland et al.; Pharmacokinetic Drug Interactions of Gefitinib with Rifampicin, Itraconazole and Metoprolol; Clinical Pharmacokinetics; vol. 44; No. 10; Jan. 1, 2005; pp. 1067-1081.
van Erp et al.; Clinical pharmacokinetics of tyrosine kinase inhibitors; Cancer Treatment Reviews; vol. 35; No. 8; Dec. 1, 2009; pp. 692-706.
International Search Report and Written Opinion for PCT/US2011/048922 dated Jun. 1, 2012.
Abstract in English for CN 103755688, publication date Apr. 30, 2014.
International Search Report and Written Opinion for PCT/EP2014/079150 dated Mar. 23, 2015.
Yap et al., "Phase I Trial of the Irreversible EGFR and HER2 Kinase Inhibitor BIBW 2992 in Patients With Advanced Solid Tumors", Journal of Clinical Oncology, 2010, vol. 28, No. 25, pp. 3965-3972.
Bennouna, "Afatanib-based combination regimens for the treatment of solid tumors: rationale, emerging strategies and recent progress", Future Oncology, 2015, p. 355-372.
Janigian, "Dual Inhibition of EGFR with Afatinib and Cetuximab in Kinase Inhibitor-Resistant EGFR-Mutant Lung Cancer with and without T790M Mutations", Cancer Discovery, 2014, p. 1036-1045.
Shaw et al. A phase I dose escalation study if BIBW 2992, an irreversible dual EGFR/HER2 receptor tyrosine kinase inhibitor, in patients with advanced solid tumors, Journal of Clinical Oncology, 2006, vol. 24, No. 18S, p. 3027.
Kris et al., JAMA, 2003, vol. 290, No. 16, pp. 2149-2158.
Therasse et al., "New Guidelines to Evaluate the Response to Treatment in Solid Tumors", Journal Nat Cancer Inst., Feb. 2, 2000, vol. 92, No. 3, p. 205-216.
Herbst et al., "Lung Cancer", New England Journal of Med., Sep. 25, 2008, 359;13, p. 1367-80.
IRESSA (gefitinib) US product label, 2003.
Soria et al., "Afatinib verse erlotinib as second-line treatment of patients with advanced squamous cell carcinoma of the lung (LUX-Lung 8): an open-label randomised controlled phase 3 trial", Lancet, Aug. 2015, vol. 16, p. 897-907.
GILOTRIF (afatinib) US product label, 2016.
Rivera et al., "Current situation of Panitumumab, Matuzumab, Nimotuzumab and Zalutumumab", Acta Oncologica, 2008, vol. 47, No. 1, pp. 9-19.
Dienstmann et al., "Necitumumab, a fully human IgG1 mAb directed against the EGFR for the potential treatment of cancer", Current Opinion in Investigational Drugs, 2010, vol. 11, No. 12, pp. 1434-1441.
Lee, Yun J., et al., "A Phase Ib/II Study of Afatinib in Combination with nimotuzumab in non-small cell lung cancer patients with acquired resistance to gefitinib or erlotinib", Clinical Cancer Research, 22(( ), 2016, p. 2139-2146.
Voigt, Rudolf, "Pharmazeutische Technologie" 9th Edition, Wilssen & Praxis, (2000), Chapter 9.3 p. 167.
Kitazaki, Takeshi et al. "Gefitinib, an EGFR tyrosine kinase inhibitor, directly inhibits the function of P-glycoprotein in multidrug resistant cancer cells" (2005) Lung Cancer, vol. 49, 337-343.

* cited by examiner

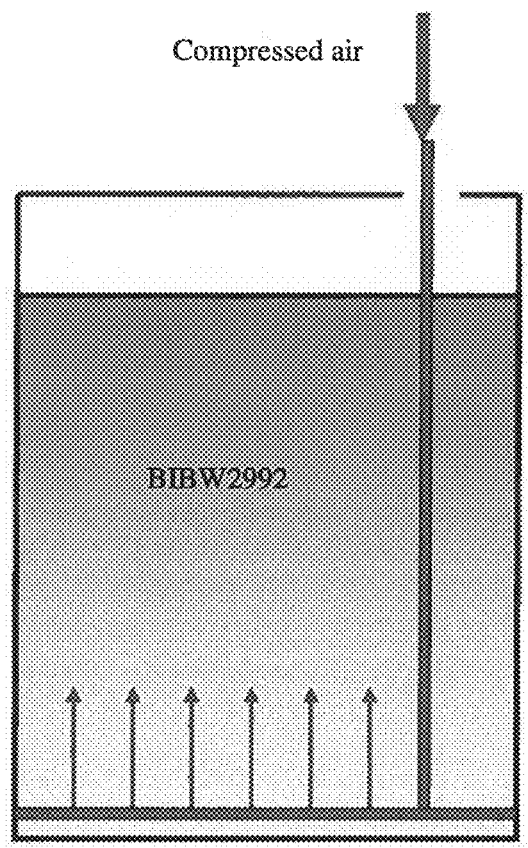
Figure 1: Drying device using compressed air

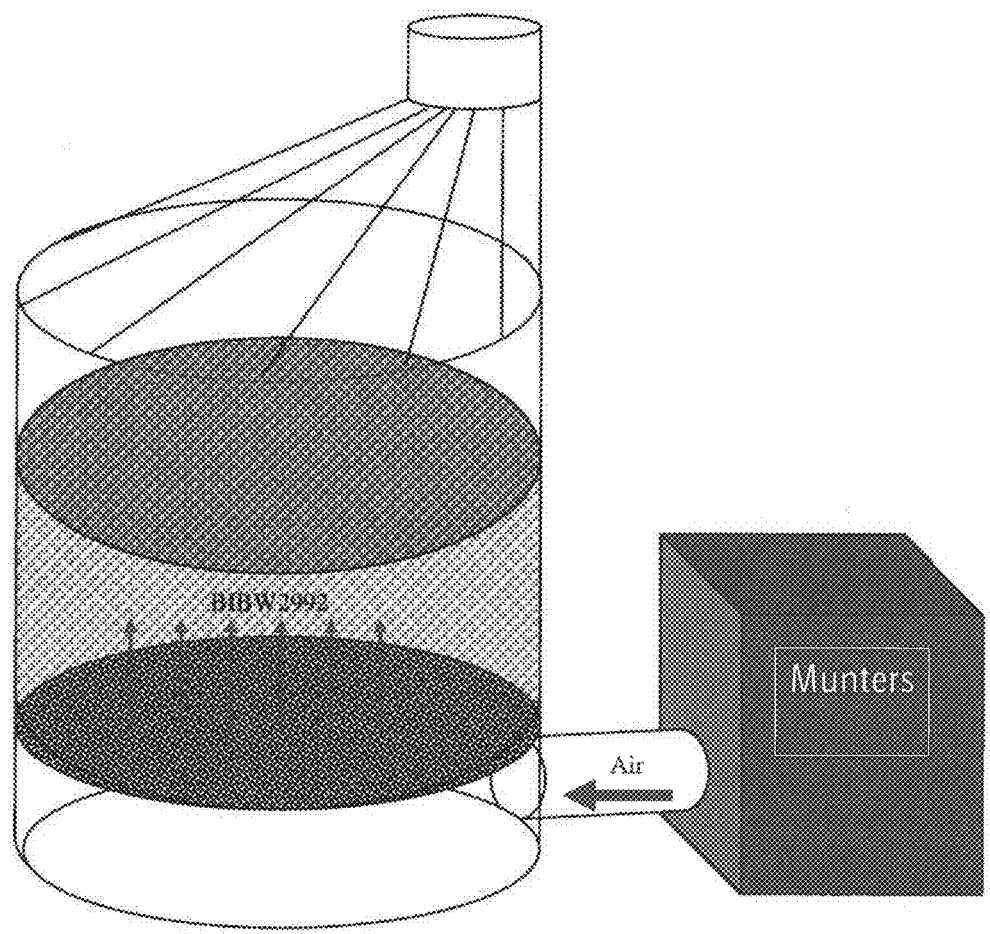
Figure 2: Munters drying device

PROCESS FOR DRYING OF BIBW2992, OF ITS SALTS AND OF SOLID PHARMACEUTICAL FORMULATIONS COMPRISING THIS ACTIVE INGREDIENT

FIELD OF THE INVENTION

The present invention relates to a drying process of BIBW 2992 or the salts thereof, preferably the dimaleate salt (abbreviated hereinafter BIBW 2992 $MA_2$), as well as of solid pharmaceutical formulations comprising BIBW 2992 or a salt thereof, and to pharmaceutical compositions comprising BIBW 2992 or a salt thereof as the active product ingredient (API), characterized by a water activity of the formulation of not more than 0.20 or a water content (Karl-Fischer) of the formulation of not more than 4.2%.

BACKGROUND OF THE INVENTION

BIBW 2992 (also named TOMTOVOK®) is known as the compound 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline,

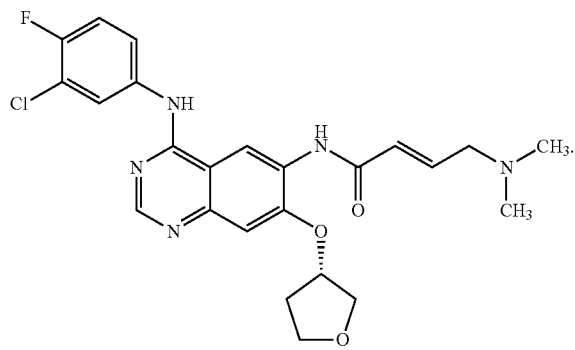

(1)

BIBW 2992 is a potent and selective dual inhibitor of erbb1 receptor (EGFR) and erbB2 (Her2/neu) receptor tyrosine kinases. Furthermore, BIBW 2992 was designed to covalently bind to EGFR and HER2 thereby irreversibly inactivating the receptor molecule it has bound to. This compound, salts thereof such as the dimaleate BIBW 2992 $MA_2$ and its crystalline modification, their preparation as well as pharmaceutical formulations comprising BIBW 2992 or a salt thereof are disclosed in WO 02/50043 and WO 2005/037824. These documents are incorporated by reference regarding these aspects.

BIBW 2992 is suitable for the treatment of tumoral diseases, hypersecretory diseases of the lungs and respiratory tract, diseases of the gastrointestinal tract, the bile duct and gall bladder. Indications to be treated with BIBW 2992 and combination treatments are disclosed in WO 2007/054550 and WO 2007/054551.

Besides the pharmacological activity of an active pharmaceutical ingredient (API) there are a variety of chemical, physical or physicochemical characteristics of the active substance relevant for the preparation of solid oral dosage forms, as oral powders, granules, pellets, tablets, capsules, chewable tablets, dispersible tablets, or lozenges. To achieve adequate formulation characteristics, as correct assay, content and mass uniformity, chemical and physical stability of the drug product and a proper dissolution rate, also the characteristics of the product intermediates have to be adequate for robust, fast and cost efficient processing.

Without being restrictive, examples of these parameters relevant for processing of the active agent (the drug substance) are the stability of the drug substance under various environmental conditions which strongly may influence the stability of the final pharmaceutical formulation (the drug product), and physical characteristics of the drug substance such as bulk densities (i.e. poured and tapped density), particle morphology, shape, the ratio of length to width for needles, size distribution, electrostatic charging and surface adhesive properties, which may vary due to precipitation and drying conditions of the drug substance. These characteristics may significantly influence key features for processing of the drug substance into a final formulation, such as flowability and compressibility.

For actives sensitive to hydrolytic degradation it is substantial to minimize access of moisture within the manufacture of the drug product up to packaging as well as to take effective measures to prevent entrance of water into the final packaging in order to achieve an adequate shelf life of the product.

BIBW 2992 is a moisture sensitive compound and can quickly hydrolytically degrade at humid conditions, e.g. in the presence of water, moisture or moisture released by further excipients in the drug product, resulting a main API degradation product by release of dimethylamine from the side chain attached to position 6 of the quinazoline.

BRIEF SUMMARY OF THE INVENTION

A first object of the present invention is directed to a process for drying of BIBW 2992 or a salt thereof, preferably BIBW 2992 $MA_2$, comprising drying with a gas which is inert towards BIBW 2992 at the drying conditions and which has a relative humidity (rh) of not more than 15%, preferably not more than 12% rh, at a temperature below 40° C., preferably below 30° C.

A second object of the present invention is directed to a process for drying of a pharmaceutical formulation containing BIBW 2992 or a salt thereof, preferably BIBW 2992 $MA_2$, as the active ingredient and at least one further excipient, with a gas, e.g. air which is inert towards the ingredients of the mentioned pharmaceutical formulation at the drying conditions, and which has a relative humidity of not more than 15%, preferably not more than 12% rh, at temperatures below 40° C., preferably below 30° C.

A third object of the present invention is a pharmaceutical composition comprising BIBW 2992 or a salt thereof, preferably BIBW 2992 $MA_2$, as an active ingredient and at least one further excipient, e.g. an oral, pharmaceutical dosage form, such as a tablet, which is characterized by a water activity of not more than 0.20, preferably of not more than 0.17, or, most preferred, of not more than 0.15.

A fourth object of the present invention is a pharmaceutical composition comprising BIBW 2992 or a salt thereof, preferably BIBW 2992 $MA_2$, as an active ingredient and at least one further excipient, e.g. an oral, pharmaceutical dosage form, such as a tablet, which is characterized by a water content (Karl-Fischer) of not more than 4.2%, preferably of not more than 4.0%, particularly of not more than 3.8%, or, most preferred, of not more than 3.7%.

DETAILED DESCRIPTION OF THE INVENTION

BIBW 2992 to be dried according to the process of the invention or referred to herein within the context of the invention includes the API in any form, e.g. in the form of the free base itself, in the form of a solvate and in the form of a salt, preferably a pharmaceutically acceptable salt.

Pharmaceutically acceptable salts are for instance selected from the group consisting of the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrolactate, hydroxalate, hydrosuccinate, hydrobenzoate and hydro-p-toluenesulphonate, preferably the hydrochloride, hydrobromide, hydrosulphate, hydrophosphate, hydromaleate, hydrofumarate and hydromethanesulphonate. In a particularity preferred embodiment with regard to any aspects of the invention BIBW 2992 is applied as its hydromaleate, preferably in the ratio BIBW 2992:maleic acid=1:2 as depicted in the formula (1a) below (also denoted herein as the "dimaleate" or BIBW 2992 MA$_2$).

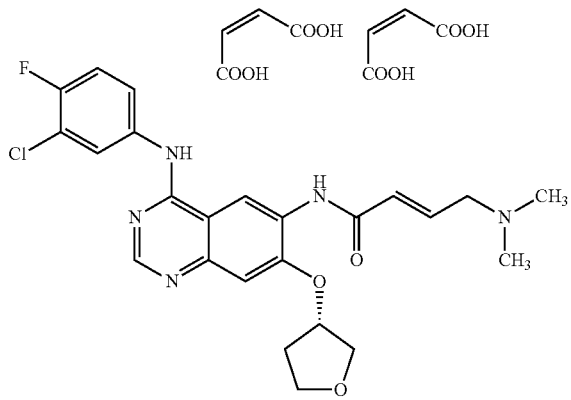

(1a)

BIBW 2992 also includes combinations with at least one pharmaceutical excipient, e.g. a pharmaceutical composition comprising BIBW 2992 in the form of the free base, in the form of a solvate or in the form of a salt as the active ingredient, as an intermediate for further processing or as a final dosage form ready for ingestion.

Preferred pharmaceutical compositions as an intermediate for further processing includes a compacted intermediate or a dry granulated intermediate comprising BIBW 2992 MA$_2$ in form of a powder obtainable by a combined compaction (either roller compaction, briquetting or slugging) or dry granulation and subsequent sieving of the compacted active, optionally in mixture with a lubricant, to adjust and equilibrate its bulk properties and therefore ensure its suitability for further processing into a finished dosage form, the intermediate and final blends prepared from said compacted (or dry granulated) intermediate, suitable for further processing in the preparation of solid oral dosage forms.

Particularly preferred pharmaceutical compositions are those comprising BIBW 2992 MA$_2$ in final dosage forms ready for ingestion, including solid oral formulations made from said compacted intermediate, from said intermediate blends or from said final blends, in powdery, compacted, granulated or compressed, form e.g.

dry powder formulations,
uncoated or coated granules,
uncoated or coated pellets, and
uncoated or film-coated tablets, e.g. prepared by direct-compression,
any of those optionally filled in capsules, e.g. hard gelatin capsules or HPMC (hydroxypropylmethylcellulose) capsules.

The process according to the present invention may be carried out by drying the sample comprising BIBW 2992 (or a pharmaceutically acceptable salt thereof) or any of the pharmaceutical compositions comprising BIBW 2992 (or a pharmaceutically acceptable salt thereof) mentioned hereinbefore, which contains humidity, e.g. water moisture from a formulation procedure, such as aqueous film-coating or adsorbed from a further excipient containing genuine non-crystalline water or moisture adsorbed from environmental air, using continuous contact of the sample with a gas flowing through which is inert towards BIBW2992 at the drying conditions and has a relative humidity of not more than 15%, preferably of not more than 12% rh, at temperatures below 40° C., preferably below 30° C., until the targeted water activity (equilibrium moisture content) in the sample is achieved. The water activity is a measure of the water that is freely available in the sample and is available for exchange with the atmosphere. A desired water activity reduces the water which may be present free or as solvate bound in excipients in the drug product and includes moisture of the form in which BIBW 2992 is present after completion of drying, e.g. 0.20 water activity and less, or Karl-Fischer water content of 4.2% and less.

The water activity mentioned in the context of the invention is meant to be determined as mentioned in the United States Pharmacopeia (USP) <1112>. Furthermore, the Karl-Fischer water content mentioned in the context of the invention is meant to be a titrimetric method (i.e. biamperometric Karl Fischer titration) specified in the United States Pharmacopeia (USP) <921>. Examples for the methods used are provided hereinafter.

It is essential that the gas used, e.g. inert gas, dried compressed or constantly supply dried air, nitrogen or carbon dioxide, has a relative humidity of not more than 15% rh, preferably not more than 12%, in order to guarantee a sufficiently high humidity gradient between the product and the drying gas. Consequently a permanent gas flow has to be assured in order to maintain the humidity gradient and achieve the targeted humidity of BIBW2992. Such could be achieved either by a continuous flow-through of dried compressed air or by continuous flow generated by ventilators (e.g using a Munters® device).

The process according to the present invention is carried out by placing the sample in a container having an inlet and an outlet opening for the supply and removal of the gas.

In one embodiment of the invention the gas stream is purged through the container and the sample as a continuous flow-through of dried compressed air with a pressure at the outlet of approximately 0.5 to 3 bar, preferably 0.8 to 1.5 bar, most preferred about 1 bar. Especially for this purpose containers with a bi-layer bottom are used, in which the upper one is perforated in order to allow the gas to pass through. The gas is introduced into the space between the two bottoms, flows through the perforated upper bottom and then through the product. Finally the gas containing moisture from the product is discharged through the outlet.

In a second embodiment of the invention the gas stream is purged through the container and the sample as a continuous flow generated by ventilators (e.g using a Munters® device) providing an air flow rate of 20-1000 ncm/h, preferably of 30-500 ncm/h, most preferred, of 40-150 ncm/h. The expression "ncm" denotes "norm cubic meter", alternatively abbreviated in the literature as "m³ (i.N.)", defining a volume of a gas under norm or standard conditions, here of 1013 mbar, a relative humidity (rh) of 0% and a temperature of 0° C.

According to any embodiment of the invention drying temperature is set in the range of 20-40° C., preferably in the range of 20-30° C., e.g. room temperature. During drying, water which may be present as solvate bound in BIBW2992 as dihydrate or Lactose as monohydrate is substantially not removed.

It has been found that at the given conditions drying has to be performed for at least 8 hours, preferably for at least 12 h, most preferred for at least 24 h, in order to achieve the targeted water activity of the formulation of 0.20 and less or Karl-Fischer water content of the formulation of 4.2% and less.

In contrast, an alternative approach to reduce moisture content as conventional drying of film-coated tablets comprising BIBW 2992 in a film-coater at temperatures clearly higher than room temperature e.g. 50° C. led only intermediately to a low level of moisture during the drying process itself. Finally the product (film-coated tablets) have to be cooled down to room temperature associated with moisture re-uptake, since the relative humidity of the cooling air is above 15% rh.

A further alternative conventional approach to reduce moisture content could be storage of BIBW 2992 bulk in close contact with desiccants. The desiccants remove unbound water from the product via physical adsorption of water. For drying of bulk products as e.g. film-coated tablet such a method requires a much longer drying time as the presented method in order to achieve the targeted moisture content and thus is unsuitable to be used in production scale.

SHORT DESCRIPTION OF THE FIGURES

FIG. 1 schematically shows a container suitable for the process according to the present invention comprising an inlet line and an outlet opening for the supply and removal of the gas, a bi-layer bottom (upper and lower bottom) connected with the inlet line, wherein the upper bottom is perforated in order to allow the drying gas to pass through the inner space of the container comprising the sample.

FIG. 2 schematically shows a container suitable for the process according to the present invention with Munters® device gas supply.

The following non-limiting examples serve to illustrate the invention:

EXAMPLE 1

50 kg of film-coated tablets containing 20 mg BIBW 2992 base each are filled into a drying container that is equipped with a double bottom, an air inlet and an air outlet. The tablets are flushed in the container with dried compressed air with relative humidity of not more than 12% and a temperature of approximately 20° C. until the water activity of the formulation is less than 0.15 or the water content (Karl Fischer) of the formulation is not more than 4.0%. Finally a water content of 3.7% (Karl Fischer) after drying was achieved.

After 6 months storage in Alu/Alu-blister at 40° C./75 rh an increase of 1.6% main API degradation product was observed.

EXAMPLE 2 (COMPARATIVE EXAMPLE)

Without initial drying film-coated tablets containing 20 mg BIBW 2992 base showed a water content of the formulation of 4.3%. After 6 months storage in Alu/Alu-blister at 40° C./75 rh an increase of 2.6% main API degradation product was detected.

EXAMPLE 3: DOSAGE FORMS COMPRISING BIBW 2992 $MA_2$ (1A) TO BE DRIED USING THE PROCESS OF THE INVENTION

In the following section the manufacturing method for dosage forms of 1a is described.

Process for Preparing Compacted Intermediates Comprising 1a

A compacted intermediate comprising 1a in form of a powder is prepared by a roller compaction step for densification of the material, combined with at least one sieving step additional to the break-up of the ribbon or briquettes, optionally in mixture with a lubricant.

The roller compaction may be carried out with
the API 1a alone or, optionally, with
a pre-blend of the API with 0 to 1.0% of a lubricant in a freefall or tumble blender to prevent major sticking on the compaction rolls.
Addition of a lubricant can be avoided if agitated API is used and kept under agitation when loading onto the roller compactor.

The API or pre-blend of the API is compacted on a conventional roller compactor
optionally with horizontally, vertically or 45° angle alignment of the compaction rolls,
which may be smooth or shaped on their surface.
The compaction force may vary
between 1 kN/cm and 20 kN/cm,
preferably between 2 kN/cm and 10 kN/cm,
at a compaction speed of the compaction rolls
between 1 rpm and 30 rpm,
preferably between 1 rpm and 10 rpm,
and a gap width between the compaction rolls
between 1 mm and 10 mm
preferably between 1 and 5 mm.

The compacted intermediate is received from the compaction rolls in form of ribbons which are directly broken up into granules by a granulation-unit with a mesh size between 0.5 mm and 1.6 mm, resulting the compacted intermediate in form of granules. In the second step subsequently the granules are sieved by a sieving machine, as e.g. an oscillating or conical sieving machine or hammer mill, with a mesh size of 0.5 to 2.0 mm, preferably about 1.0 mm, resulting the compacted intermediate in the form of a powder. Optionally a second sieving step is performed, whereas this one should be conducted with a mesh size of 0.3 to 0.5 mm, preferably about 0.5 mm.

Process for Preparing Intermediate Blends and Final Blends

Intermediate Blends:

Any intermediate blends comprising 1a in form of a powder are prepared by mixing the API with carrier, binder or combination thereof, glidants, colorants and solid flavours in a freefall or tumble blender.

Final Blends:

Oral Powders:

The intermediate blend comprising 1a in form of a powder is mixed with carriers, binders, glidants, colorants and solid flavours in a freefall or tumble blender.

Oral Granules:

The intermediate blend comprising 1a in form of a powder is mixed with fillers carriers, binders, solid binders, colorants and solid flavours in a freefall or tumble blender. The blend is compacted on a roller compactor and broken up by a granulation-unit with a mesh size of about 2 mm.

Pellets in Capsules:
The intermediate blend comprising 1a in form of a powder is mixed with solid polyethylene glycol and microcrystalline cellulose and extruded through a heated extruder. The pellets are spheronized. After spheronization the resulting pellets are filled in capsules, e.g. hard gelatin or HPMC capsules.

Tablets and Filmcoated Tablets:
The intermediate blend comprising 1a in form of a powder is mixed with fillers carriers, binders, glidants and disintegrants in a freefall or tumble blender. Finally the lubricant is added to the main-blend and further mixing is performed.

Process for Preparing the Solid Oral Formulations

Oral Powders:
The final powder blend is filled in sachets.

Oral Granules:
The granules are filled in sachets.

Pellets in Capsules:
After spheronization the resulting pellets are filled in capsules, e.g. hard gelatin or HPMC capsules.

Tablets and Filmcoated Tablets:
The final blend is compressed on a suitable tablet press to produce tablets by an adequate compression force to obtain the quality parameters with regard to resistance to crushing, tablet height and disintegration.

Optionally the tablet cores are coated in a drum-coater by a coating suspension e.g. using a Glatt GC 550/750 or GC 1250 coater.

TABLE 1

Exemplary composition of solid Tablets comprising 1a

| Ingredient | % per tablet | Formulation A mg per tablet | B mg per tablet | C mg per tablet | D mg per tablet | E mg per tablet |
|---|---|---|---|---|---|---|
| 1a, un-milled (corresponding to free base 1) | 16.42 | 29.5600 (20.0000) | 44.3400 (30.0000) | 59.1200 (40.0000) | 73.9000 (50.0000) | 103.4600 (70.0000) |
| Lactose monohydrate | 68.81 | 123.8600 | 185.7900 | 247.7200 | 309.6500 | 433.5100 |
| Microcrystalline cellulose | 10.27 | 18.4800 | 27.7200 | 36.9600 | 46.2000 | 64.6800 |
| Crospovidone | 2.00 | 3.6000 | 5.4000 | 7.2000 | 9.0000 | 12.6000 |
| Colloidal anhydrous silica* | 0.50 | 0.9000 | 1.3500 | 1.8000 | 2.2500 | 3.1500 |
| Magnesium stearate | 2.00 | 3.6000 | 5.4000 | 7.2000 | 9.0000 | 12.6000 |
| Total | 100.00 | 180.0000 | 270.0000 | 360.0000 | 450.0000 | 630.0000 |

Formulations A, B and C, D and E are tablets which can be coated with a film-coat according to Table 2.

TABLE 2

Exemplary composition of filmcoatings for Formulation A-E

| Ingredient | Coating for Formulation A | B | C | D | E |
|---|---|---|---|---|---|
|  | mg per tablet | | | | |
| Hypromellose | 2.5000 | 3.5000 | 4.0000 | 5.0000 | 6.0000 |
| Polyethylene glycol 400 | 0.5000 | 0.7000 | 0.8000 | 1.0000 | 1.2000 |
| Titanium dioxid | 1.1300 | 0.6825 | 1.8080 | 0.9750 | 1.1700 |
| Indigo Carmine aluminum lake | 0.0700 | 0.2450 | 0.1120 | 0.3500 | 0.4200 |
| Talcum | 0.6500 | 1.6625 | 1.0400 | 2.3750 | 2.8500 |
| Polysorbate 80 | 0.1500 | 0.2100 | 0.2400 | 0.3000 | 0.3600 |
| Purified water (volatile component) | — | — | — | — | — |
| Total | 5.0000 | 7.0000 | 8.0000 | 10.0000 | 12.0000 |

EXAMPLE 4: WATER CONTENT/BIAMPEROMETRIC KARL FISCHER TITRATION

Solvents and Reagents

Solvent: Methanol, anhydrous

Titrant: Hydranal® Composite 1[*]

[*] Hydranal® is a registered trademark of Sigma-Aldrich Biotechnology LP and Sigma-Aldrich Co. Hydranal® Composite 1 is a single component pyridine-free Karl Fischer reagent, Sigma-Aldrich® product ID 34827.

Procedure

Apparatus: Karl Fischer apparatus

Syringe 5.0 mL (Hamilton)

| Parameter: | | |
|---|---|---|
| Titrant | Minimum volume increment | Stop drift |
| Composite 1 | 6 µL | 70 µL/min |

Determination: Four film-coated tablets are accurately weighed into a 50 mL injection vial, immediately 25 mL anhydrous methanol is added and the vial will be directly tightly closed with a septum and a crimp cap. After 3 hours of shaking (automated equipment) and about 20 hours of sedimentation time a 4.0 mL aliquot is removed with a syringe and transferred into the titration vessel, which contains about 30 mL pre-titrated methanol. Blank titration of extraction vial:

25 mL of anhydrous methanol is added into a 50 mL injection vial (n=2) and the vial will be directly tightly closed with a septum and a crimp cap. After 3 hours of shaking (automated equipment) and about 20 hours of sedimentation time a 4.0 mL aliquot is removed with a syringe and transferred into the titration vessel, which contains about 30 mL pre-titrated methanol.

| Sample preparation/determination scheme | |
|---|---|
| number of separately prepared samples | 1 |

Film-coated tablets should be handled open as short as possible.

Water content [%] is calculated as follows:

Error!

a=volume of Karl Fischer solution required to titrate the test sample [mL]

b=average volume of Karl Fischer solution required for blank titration [mL]

F=factor of titrant [mg water/mL]

WtTS=weight of test sample [mg]

EXAMPLE 5: WATER CONTENT/DETERMINATION OF WATER ACTIVITY

Procedure

Apparatus: e.g. Novasina Labmaster $a_w$

| Parameter: | Temperature | 25° C. |
|---|---|---|
| | Obs. Time aw | 1 min |
| | Obs. Time temp. | 1 min |

Determination: Fill 20 film-coated tablets (20 mg, 30 mg, or 40 mg) or 15 film-coated tablets (50 mg) into a sample cup Immediately place the sample into the measurement chamber. Close the instrument and start the measurement with the Start/Stop button. When the $a_w$-value becomes "stable", the green LED lights up and the $a_w$-value is displayed.

| Sample preparation/determination scheme | |
|---|---|
| number of determinations | 1 |

Film-coated tablets should be handled open as short as possible.

The invention claimed is:

1. A pharmaceutical composition comprising BIBW 2992 or a salt thereof as the active product ingredient (API) and at least one further excipient, characterized by a water activity of the formulation of not more than 0.17.

2. A pharmaceutical composition comprising BIBW 2992 or a salt thereof as the active product ingredient (API) and at least one further excipient, characterized by a water content of not more than 4.0% as measured by Karl Fischer titration method.

3. The pharmaceutical composition according to claim 1, wherein the pharmaceutical composition is an uncoated or film-coated tablet.

4. The pharmaceutical composition according to claim 1, wherein the pharmaceutical composition is selected from uncoated and film-coated tablets comprising BIBW 2992 dimaleate salt as the active product ingredient (API) and each of the tablets is a composition selected from the group consisting of compositions A, B, C, D and E:

| | | Formulation | | | | |
|---|---|---|---|---|---|---|
| | | A | B | C | D | E |
| Ingredient | % per tablet | mg per tablet | mg per tablet | mg per tablet | mg per tablet | mg per tablet |
| BIBW 2992 MA$_2$, un-milled (corresponding to free base BIBW 2992) | 16.42 | 29.5600 (20.0000) | 44.3400 (30.0000) | 59.1200 (40.0000) | 73.9000 (50.0000) | 103.4600 (70.0000) |
| Lactose monohydrate | 68.81 | 123.8600 | 185.7900 | 247.7200 | 309.6500 | 433.5100 |
| Microcrystalline cellulose | 10.27 | 18.4800 | 27.7200 | 36.9600 | 46.2000 | 64.6800 |
| Crospovidone | 2.00 | 3.6000 | 5.4000 | 7.2000 | 9.0000 | 12.6000 |
| Colloidal anhydrous silica | 0.50 | 0.9000 | 1.3500 | 1.8000 | 2.2500 | 3.1500 |
| Magnesium stearate | 2.00 | 3.6000 | 5.4000 | 7.2000 | 9.0000 | 12.6000 |
| Total | 100.00 | 180.0000 | 270.0000 | 360.0000 | 450.0000 | 630.0000 | and wherein said film coat, if present, is selected from the group consisting of formulations A, B, C, D and E:

| | Coating for Formulation | | | | |
|---|---|---|---|---|---|
| | A | B | C | D | E |
| Ingredient | | | mg per tablet | | |
| Hypromellose | 2.5000 | 3.5000 | 4.0000 | 5.0000 | 6.0000 |
| Polyethylene glycol 400 | 0.5000 | 0.7000 | 0.8000 | 1.0000 | 1.2000 |
| Titanium dioxide | 1.1300 | 0.6825 | 1.8080 | 0.9750 | 1.1700 |
| Indigo Carmine aluminum lake | 0.0700 | 0.2450 | 0.1120 | 0.3500 | 0.4200 |
| Talcum | 0.6500 | 1.6625 | 1.0400 | 2.3750 | 2.8500 |
| Polysorbate 80 | 0.1500 | 0.2100 | 0.2400 | 0.3000 | 0.3600 |

-continued

| Ingredient | Coating for Formulation | | | | |
|---|---|---|---|---|---|
| | A | B | C | D | E |
| | mg per tablet | | | | |
| Purified water (volatile component) | — | — | — | — | — |
| Total | 5.0000 | 7.0000 | 8.0000 | 10.0000 | 12.0000. |

5. The pharmaceutical composition according to claim 4, wherein each of the tablets is a composition selected from the group consisting of compositions A, B, C and D.

\* \* \* \* \*